United States Patent [19]

Cais et al.

[11] 4,454,231

[45] Jun. 12, 1984

[54] METHOD AND DEVICE FOR MASS TRANSFER OPERATION IN IMMUNOASSAYS AND OTHER APPLICATIONS

[75] Inventors: Michael Cais; Moshe Shimoni, both of Haifa, Israel

[73] Assignee: Technion Research and Development Foundation, Ltd., Haifa, Israel

[21] Appl. No.: 212,806

[22] Filed: Dec. 4, 1980

[30] Foreign Application Priority Data

Dec. 12, 1979 [IL] Israel ........................................ 58943

[51] Int. Cl.$^3$ ..................... G01N 33/58; G01N 35/00; B65D 71/00
[52] U.S. Cl. .................................... 436/500; 436/510; 436/542; 436/800; 436/801; 436/804; 436/808; 436/810; 436/811; 436/816; 436/817; 435/7; 422/59; 422/61; 422/68
[58] Field of Search ..................... 424/1, 12; 23/230 B; 422/61, 59, 68; 435/7; 436/542, 500, 510, 800, 801, 804, 808, 810, 811, 816, 817

[56] References Cited

U.S. PATENT DOCUMENTS

| | | | |
|---|---|---|---|
| 2,524,362 | 10/1950 | Smith | 128/220 |
| 3,068,855 | 12/1962 | Furlong, Jr. | 422/61 |
| 3,449,081 | 6/1969 | Hughes | 422/61 |
| 3,992,150 | 11/1976 | Retzer | 422/61 |
| 4,021,352 | 5/1977 | Sarstedt | 210/359 |
| 4,071,319 | 1/1978 | Nugent | 422/61 |
| 4,087,248 | 5/1978 | Miles | 424/1 |
| 4,197,287 | 4/1980 | Piasio et al. | 424/1 |
| 4,254,082 | 3/1981 | Schick et al. | 422/61 |

Primary Examiner—Christine M. Nucker
Attorney, Agent, or Firm—Schwartz, Jeffery, Schwaab, Mack, Blumenthal & Koch

[57] ABSTRACT

The present invention relates to a new technique and device for mass transfer of one or more components from one liquid phase to another liquid phase, involving a physical separation of said two phases.

According to the new technique, the mass transfer and physical separation are carried out in the same device. The device consists of a mixing-reservoir into which is fitted snugly a mixer-separator, having a channel in the vertical axis of the mixer-separator. The two substantially immiscible liquid solutions are introduced into the mixing reservoir, the phases are thoroughly mixed, by moving the mixer-separator in and out the mixing reservoir. After the spontaneous separation into an upper and lower phase, the upper phase is removed by pushing in the mixer-separator said upper phase being accumulated in a collecting container.

The new technique and device can be successfully utilized in the general field of liquid-liquid extraction and particularly applied in immunoassays, where the two basic operations of mass transfer and physical separation of fractions are required.

32 Claims, 6 Drawing Figures

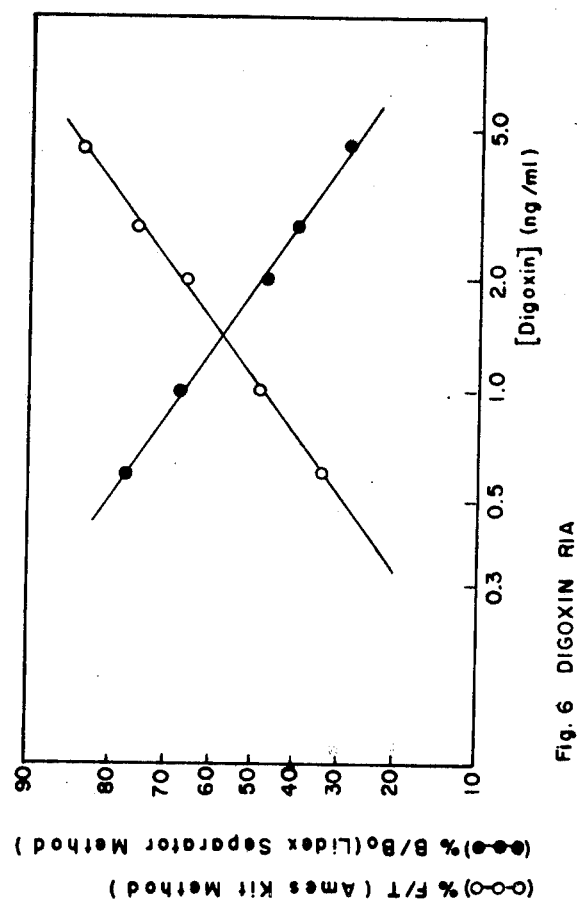
Fig. 6 DIGOXIN RIA

METHOD AND DEVICE FOR MASS TRANSFER OPERATION IN IMMUNOASSAYS AND OTHER APPLICATIONS

The present invention relates to a new technique for mass transfer operations. More particularly the invention relates to a new technique and device for carrying out the transfer of one or more components from one liquid phase to another liquid phase, the two phases being substantially immiscible.

Mass transfer phenomena are to be found every where in nature and are important in all branches of science and engineering. The phrase "mass transfer" refers to the motion of molecules or fluid elements caused by some form of potential or "driving force". It includes molecular diffusion, transport by convection and simple mixing. Mass transfer is involved wherever a chemical reaction takes place, whether in an industrial reactor, a biological system or a research laboratory. The reacting substances must come together if the reaction is to proceed. In many cases the reaction slows or stops if the reaction product (or products) is (are) not removed. The rate of mass transfer may completely determine the chemical conversion when reactants must move from one phase to another in order that reaction may occur. In the case of a reversible reaction, the conversion is improved if the desired product is continuously removed by mass transfer to a second phase in which no reaction takes place. Furthermore, the relative rates of mass transfer of the several reacting and product species can greatly affect the selectivity when competing reactions are involved.

In principle, mass transfer operations and separations can be envisaged to occur between a stationary immobilized phase and a mobile liquid phase such as in ion-exchange processes or between two liquid phases such as in liquid-liquid extraction processes. It is well-known that the separation between said phases, constitutes one of the most important and critical steps in numerous laboratory and industrial processes.

Liquid-liquid phase operations in which mass-transfer is involved, are generally carried out in vessels based on the principle that after an intimate mixing or contact of one phase with the other, the two phases are allowed to separate and respectively removed. The known laboratory vessel used for this purpose is a separatory funnel. One of the disadvantages of the separatory funnel is the notorious manual operation required in separating the two phases. On commercial scale there are known two main types of equipment: (1) mixers-settlers and (2) columns. Both types of equipment attempt to secure a large contact area between the phases since the rate of transfer of the distributed component is directly proportional to this area. Differentiation between the various types of equipment is based on the method employed for contacting the liquid phases. Mixing the two phases by subdividing and dispersing one phase, forms new surfaces with rapid transfer of the solute across the large contact area. The ease of mixing depends upon the interfacial tension between the two phases, the relative densities of the two phases and the viscosity of each phase. Separation of the two phases after they have been brought into contact may be accomplished by gravity or by centrifugal force. The ease of separation of the two phases depends primarily upon the difference in density of the two phases and their viscosities and may be appreciably affected by the presence of impurities which may stabilize emulsions. This is the case with mixers-settlers.

An alternative procedure for obtaining a large contact area, is to have one phase flow past the other but without any attempt to mix the two phases. The equipment used to contact the two phases also acts as the separator, and mixing of the two phases is undesirable. This method depends on the increased length of the path of flow to obtain a large contact area and usually requires less energy consumption than when the two phases are mixed as in the previous type of equipment. Such an extended contact area between phases may be obtained by flowing the two liquid phases countercurrently or concurrently in horizontal tubes or ducts with the less dense phase flowing in the top section of the tube, or in vertical tubes or ducts with the more dense phase flowing down the wall of the tube while the less dense phase flows upward through the centre of the tube. In both the horizontal and vertical type of equipment the extended contact area is obtained by having the equipment of sufficient length. This is the case with columns. Both types of liquid-liquid extraction equipment suffer from disadvantages. Thus in case of mixers-settlers, during the agitation, whereby one of the liquids is dispersed in the other one, the intensive agitation or turbulent flow generally makes the subsequent separation in the settler of the liquid phases difficult owing to the small size and great stability of the droplets of the dispersed phase. In consequence the separation is very slow and requires large vessels. In case of columns, the capacity of the equipment is limited by the fact that the flow rates of both phases must be low enough to prevent mixing of the phases since both the contacting and the separation of the phases occur in the same piece of equipment. A general conclusion which can be drawn on the principle of mass transfer operation is the importance of the thorough mixing of the phases in order to obtain an efficient transfer of one or more components from one phase to another.

To the best of our knowledge there is no prior art on the method of mass transfer carried out in accordance with the present invention.

An ampoule syringe device including a cylindrical member having a hollow piston which is displaceable in the cylindrical member, slidably engaging the inner wall of the ampoule, is described in the U.S. Pat. No. 2,524,362. When the piston is pushed into the cylindrical member, the liquid flows through the axial hollow passage in the piston and it ejects through a needle at the end of said ampoule.

Based on the same principle, it is disclosed in the U.S. Pat. No. 3,512,940, a test tube filter device in which the piston described above, has been replaced by a hollow plunger which has a porous bottom portion to serve as a filter. A specific application using the principle of said device, has been later on described for separation of blood fractions in a number of U.S. patents and German patent applications. A typical illustration of one of these publications are the German specifications 2,415,618 and 2,454,918 (or their corresponding U.S. Pat. No. 4,021,352 and U.K. Pat. No. 1,508,844). According to these patents, the coagulated blood, which is separated by precipitation or centrifugation in the higher density fraction of the red blood cells and the lower density blood plasma are placed in a cylindrical vessel. A hollow piston, having at its lower part a disk such as sintered glass, is pushed downwardly into the cylindrical vessel until it is above the interface between the two fractions without reaching said interface. In order to be able to collect the lower density blood fraction (plasma) flowing through the upper opening of the piston, a receiving vessel is provided above the cylindrical vessel. Special care has to be used in operating this device to avoid mixing of the two phases during the downward movement of the piston and consequently only a partial removal of the plasma can be achieved. It is an object of the present invention to provide a new method for carrying out mass transfer operation and physical separation on two liquid phases in the same piece of equipment. It is another object of the present invention to provide a simple device for mass transfer and physical separation of two liquid phases which is capable of extremely wide versatility and application to both laboratory and industrial operations either on a small size scale involving microliters volumes or on a large size scale involving hundreds or even thousands of liters. It is yet another object of the present invention to provide a new method for carrying out mass transfer operation and physical separation of two liquid phases in the same piece of equipment, in a quantitative manner. Thus the invention consists in a novel device for carrying out mass transfer operation of one or more components from one liquid phase to another liquid phase involving a physical separation of said two phases, both operations being carried out in the same device, which consists of a mixing-reservoir (A) into which is fitted snugly a mixer-separator (B) having at least one channel (C) traversing the vertical axis of the mixer-separator (B), the latter being shaped at its upper end in the form of a collecting container (E) into which is accumulated and physically transposed the upper liquid phase from mixing-reservoir (A) aspirated through channel (C) when the mixer-separator (B) is pushed into the mixing-reservoir (A). The mixing-reservoir (A) may be of any suitable geometrical shape. According to the shape of the mixing-reservoir (A), the mixer-separator (B) will possess a corresponding shape.

The novel device according to the present invention has a wide versatile utility in various processes which involve mass transfer operations. Its applicability will be hereinafter illustrated for solvent extraction and immunoassay technique with stress on the latter, although it should be clearly understood that this description is non-limiting and is not meant in any way to restrict the applicability of the novel device only to immunoassay. In our previous U.S. patent application Ser. No. 124,691, it was disclosed the use of liquid-liquid extraction technique for specific binding assay. According to the invention described therein, it was found that by the use of an appropriate solvent and under specific conditions, a general method could be devised for separating the bound and free ligands in immunoassays, without adversely affecting either the binding ability of the binding protein or the binding protein-ligand equilibrium. As mentioned in said patent application, the method is in particular suitable for radioimmunoassay for those cases wherein no physical separation should be carried out, the counting of the gamma-radiating isotope being carried out in the respective bound or free phase. However in any non-homogeneous immunoassay it is generally required a separation of free labelled antigen from that which is bound to specific antibody. The ideal method should provide not only a clear separation of these components, but be uninfluenced by biological fluids and other nonspecific substances in the reaction mixture. From the prior art there are known the following categories of separation methods for the bound and free fractions:

(1) Electrophoretic and chromatoelectrophoretic methods.
(2) Gel filtration.
(3) Non-specific precipitation of hormone-protein complexes.
(4) Immunoprecipitation of soluble hormone-protein complexes.
(5) Solid-phase absorption of hormone, and
(6) Solid-phase absorption of antibody.

All the above methods suffer of very serious disadvantages. Thus, chromatoelectrophoresis is demanding of space and technician time. Clear separations and best results are obtained, when said separations are carried out in cold rooms or large refrigerator which may not be always available. Strip counters, required in this method, are prone to mechanical failures and most of them perform poorly with Iodine-125. Since most papers have a limited capacity, generally below 200 $\mu$l, one requires high specific activities of labelled hormone for an accurate counting.

Gel filtration is impractical because the preparation of individual columns is time consuming and space requiring. Moreover the collection of effluents from the columns requires technician attention.

In non-specific precipitation of hormone-protein complexes considerable amounts of free antigen can be occluded in the precipitate and slight changes in conditions will alter the degree of separation. The technician time required even for improved variations of this method appears to be greater than for some of the other methods considered and the published results do not seem sufficiently improved to warrant acceptance of this method.

Immunoprecipitation of antigen-antibody complexes has many disadvantages:
(i) Skill and care are required in aspiration or decantation of the supernatant solution. Occasionally precipitate may be trapped in a fibrin web at the meniscus and inadvertently discarded.
(ii) Human serum may interfere with the second antibody reaction in a number of ways. Some second antibodies will cross-react sufficiently with human gamma globulin so that the precipitation of first antibody is impaired. There can be serious variations in the degree of immunoprecipitation between serum and heparinized plasma.

Methods based on solid phase absorption of free antigen e.g. use of charcoal, resin, silica, florisil etc., suffer from the fact that the bound antigen-antibody complex may also be bound on the solid absorbent. A recent elegant method in the solid phase absorption of antibody is absorption of antibodies to plastic tubes. Accordingly a number of coated tubes are prepared in advance. The preparation and storage of large numbers of such tubes is a serious drawback in addition to the fact that these tubes are sensitive to variations in serum protein content. The new method according to the present invention is very simple to be carried out giving very accurate results. Furthermore, in view of the unexpensive price of the entire device, it can be for one-time use.

The method for utilization of the present invention is very simple. Let us consider, for example an aqueous solution containing a solute which is soluble in some organic solvent which is not miscible with water. This aqueous solution is placed into the mixing-reservoir (A)

so that it occupies about one fourth the volume of the mixing-reservoir (A). A suitable organic solvent which is not miscible with water is added to the mixing-reservoir (A). The amount of organic solvent added can be varied as required in accordance with the volume capacity of the mixing-reservoir. The specific gravity of the solvent can be greater or smaller than that of the aqueous solution. The two phases are then thoroughly mixed, by moving the mixer-separator in and out through the mixing-reservoir (A). If desired, this mixing may be also obtained by means of a vibrator mixer or magnetic stirrer or any other convenient mixing device, for a short period of time. After the mixing operation, the system is allowed to stand for an appropriate period of time, wherein the two non-miscible phases—upper phase and lower phase—are obtained. The mixer-separator (B) is pushed in, the liquid upper phase is entering through the channel C into the collecting container (E). The mixer-separator (B) is pushed in until it reaches the interface, thus removing completely the upper phase containing the solute previously present in the aqueous phase. The upper phase thus separated can be subsequently transferred to a suitable measuring device to determine the quantity of solute from the lower phase transferred into the upper phase. The same measurement operation can be carried out for the lower phase left in the mixing-reservoir (A). When the solute originally present in the aqueous phase is a gamma-emitting radioisotope, the operation is carried out as above, the whole system being placed in the well of a gamma-counter instrument so that only the radiation emitting from the phase-remaining in the mixing-reservoir (A) is counted. Since the total radiation count would be known in advance, the count remaining in the lower phase of mixing-reservoir (A) will give the degree of partition of the gamma-emitting radiosotope solute between the two phases. This method of analysis is in particular useful when applied to the development of immunoassays for the detection of minute concentrations of chemical substances in biological fluids. From the known nomenclature of these chemical substances the following groups can be envisaged for their analysis:

Alkaloids, such as:
  morphine, codeine, dihydrocodeine, heroin, oxymorphone, metopon, pholcodine, etc.
Barbiturates, such as:
  Veronal, luminal, seconal, phenobarbital, barbital, etc.
Steroids, estrogens such as:
  $\beta$-estradiol, estrone, estriol, 17$\alpha$, ethyinyl estradiol etc., androgents, progestogens; adrenocortical hormones, etc.
Cannabinoids and their metabolites.
Vitamins, such as:
  Carothene, riboflavine, thiamine, niacin, ascorbic acid, tocopherol, phytyl-1,4-naphtoquinone, etc.
Amino acids and polypeptides.
Sugars, including saccharides and polysaccharides.
Tranquilizers, such as: meprobamate, valium, oxazepam, phenotiazines, etc.

In addition to the above haptens other miscellaneous compounds such as cocaine, prostaglandin, antibiotics such as penicillin, chloromycetin, actinomycetin and nucleic acids and nucleotides; insecticides, fungicides, bacteriocides and nematocides such as malathion, carbamates, etc. can also be assayed with the method according to the present invention. In general, antigens, haptens and their antibodies, hormones, vitamins, drugs, metabolites and their receptors and binding materials may be determined using the present method.

Among the particular constituents to be determined the following can be mentioned:
Compensated $T_4$;
Cortisol;
Digoxin;
Folate;
h G H;
$T_3$ Uptake;
Insulin;
Triiodothyronine;
Thyroxine (Total $T_4$);
T S H.

The method according to the present invention is also particularly suitable in the case when the labelling agent is a fluorescent label, the measurements being carried out with a suitable spectrometer. When the labelling agent in the assay is a gamma-emitting radiosotope such as Iodine-125 and the upper phase is an organic solvent, the aqueous phase present in the mixing-reservoir A after the separation by the mixer-separator B, will contain the antibody-antigen complex and the whole device can be placed in the well of the gamma-counter such that only the lower phase will be counted in the instrument. The same applies when the lower phase is an organic solvent, in which case placing the whole device in the well of the gamma-counter, will count the free unbound ligand transferred to the organic solvent.

The method is applicable for any immunoassay technique such as radioimmunoassay, free radical assay, fluorescence immunoassay, enzyme immunoassay or metalloimmunoassay (as described in the U.S. Pat. No. 4,205,952.) It is in particular most useful to use the device according to the present invention in the various kits available on the market for these techniques.

Another use envisaged for the device according to the present invention is in the separation of free antigen from bound antigen-antibody complex in the case of proteins, cells and other high molecular weight compounds if one uses two water soluble but mutually incompatible polymers to induce unmixing. This generates two aqueous phases between which various species may distribute. Such a phenomenon has been described in the literature (P. A. Albertson et. al., Nature, 184, 1465 1959; G. Johnson et. al., Hr. J. Biochem., 33, 379, 1973). Incompatible pairs of polymers are numerous (see for example A Dobry et. al., J. Polym.Sci. 2, 90, 1947). The novel device and technique according to the present invention can then be applied to separate the two unmixed aqueous phases as already described above.

The method and device are also highly suitable for use in atomic absorption spectrometry for analysis of trace metals. It is often necessary to use an extraction procedure in which the organic solvent contains a chelating agent for extraction of the metal ion from the aqueous medium. The use of the novel device according to this invention provides a very simple and efficient method for the extraction procedure and following the separation of the organic phase in the collecting-container E of the device, it is possible to use this organic phase directly for the atomic absorption measurements. This device could be easily incorporated into automatic systems for sample injection into atomic absorption spectrometers.

The new device and method according to the present invention is technically simple, expeditious and inexpensive and should be considered as an ideal method in liquid-liquid extraction in general and in immunoassay in particular. In ordr to emphasize the long felt need in the art for the device and technique described above, it would be worthwhile to quote from a well-known specialist text-book "Principles of competitive protein-binding assays" (W. D. Odell and W. H. Daughaday, Editors), J. P. Lippincott Co., Philadelphia and Toronto, 1971, Chapter XI, page 303:

"The fact that so many different separation techniques have been proposed is indication of some dissatisfaction with existing methods".

It appears that the novel device and technique according to the present invention comes nearest to the requirements of the ideal method than any of the existing prior art methods.

Figure 1:
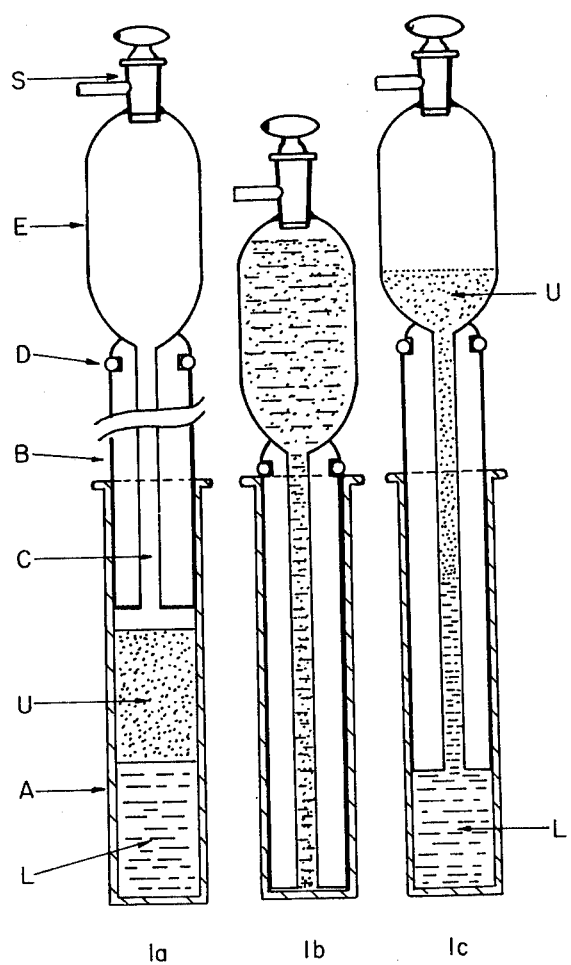
FIG. 1 illustrates the new separator system for the present invention with the individual components making up the system shown as FIGS. 1a–c.

The versatility of the device according to the present invention will be hereafter described in a more detailed manner by the attached figures: FIG. 1 illustrates schematically one of the embodiments. The device consists of four main components: mixing-reservoir (A), mixer-separator (B), collecting-container (E) and stopper (S). The stopper (S) can be either in a closed or opened position. FIG. 1(a) illustrates the device with the two liquid phases: upper (U) and lower (L) as present before the mass transfer operation. FIG. 1(b) illustrates the mixer-separator (B) pushed in fully into the mixing-reservoir (A) whereby the two phases are intimately mixed together. During the in and out movements of the mixer-separator (B), the stopper (S) is in the closed position. This allows the formation of vacuum in the mixing-reservoir (A) and increased pressure in the collecting container (E). Combination of these two effects provides a highly efficient mixing and a corresponding highly efficient mass transfer operation. At the end of the mixing operation, the mixer-separator (B) is allowed to remain in the upper position (as in FIG. 1a), the stopper (S) turned in the open position to release air pressure and the mixed liquids are allowed to spontaneously separate into an upper and lower phase. FIG. 1(c) illustrates the device wherein the mixer-separator (B) has been pushed into the mixing-reservoir (A) after the two liquid phases separated into an upper (U) and lower (L) phase. The mixer-separator (B) can be pushed in, to a desired level, so that little or no upper phase is left in the channel (C). With the stopper (S) in the open position the upper liquid phase (U) can be poured out into any other container as desired. None of the phases remaining in the channel (C) will pour out during this removal of the upper phase (U), because of the vacuum generated in the mixing-reservoir (A).

Figure 2:
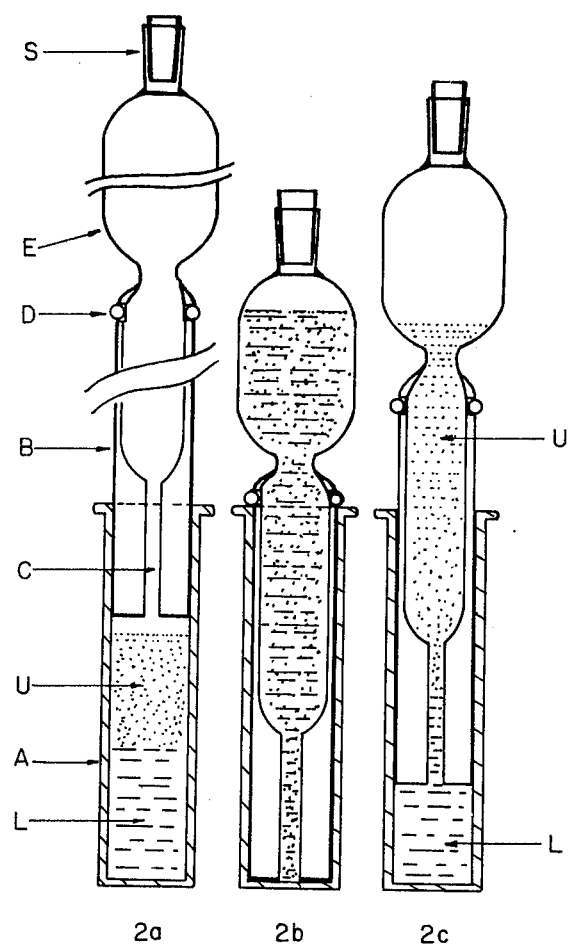
FIG. 2 shows a variation of the device, its operation being shown in FIGS. 2a–c.
Figure 3:
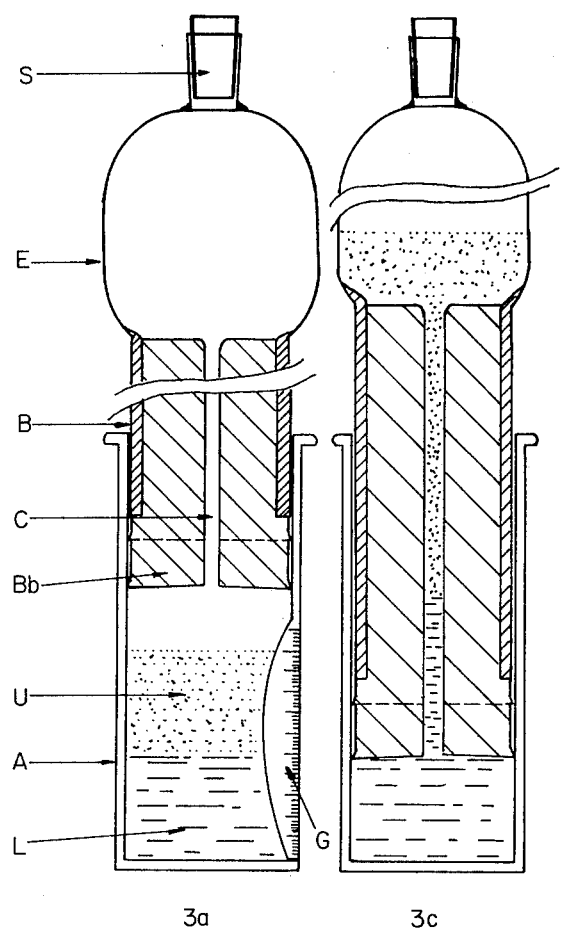
FIG. 3 shows the operation of the device of FIG. 1 in its different positions.

FIG. 2 shows a variation of the device illustrated in FIG. 1, wherein the channel (C) does not traverse the entire length of the mixer-separator (B). FIGS. 2a, 2b and 2c, illustrate the operation of the device as described for FIG. 1. The device illustrated in these figures also show a different type of the stopper (S). FIG. 3 represents another embodiment of the device according to the present invention, wherein only the lower part (Bb) of the mixer-separator (B) is snugly fitted into the mixing-reservoir (A). In addition, the mixing-reservoir (A) is shown to have graduated scale (G) for volume measurements. Of course that this graduation can also be carried out to the embodiments illustrated in the other Figures. The snugly fitting part (Bb) which is an integrated part of the mixer-separator (B) could also be incorporated in such a manner that it could be replaceable either by screwing mode or any other means. The operation of the device illustrated in FIGS. 3a and 3c, correspond to those in FIGS. 1a, 2a, 1c and 2c respectively.

Figure 4:
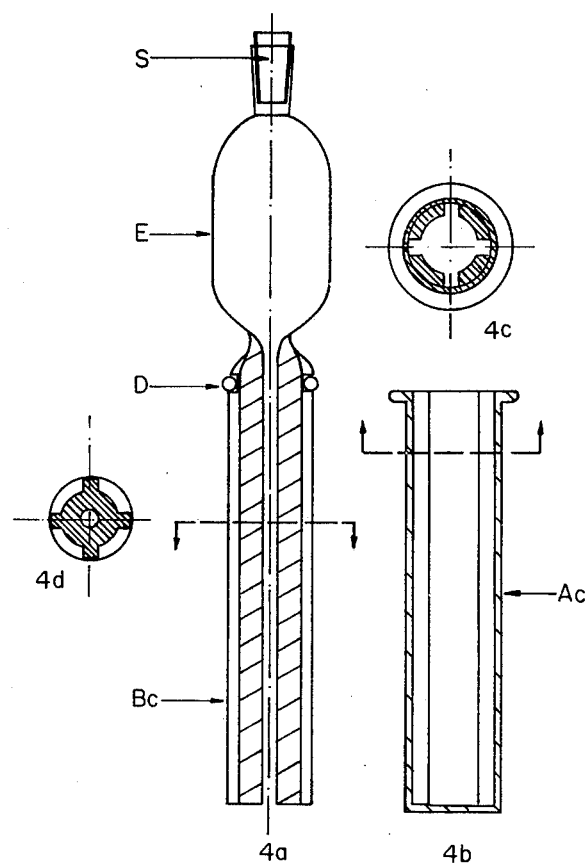
FIG. 4 illustrates another embodiment of the device including an additional construction as appears in FIGS. 4a–d.

FIG. 4 represents another embodiment of the device according to present invention. This embodiment illustrates an additional construction which purpose is to further facilitate the smooth gliding of the mixer-separator (B) into the mixing-reservoir (A). In particular this embodiment will be suitable in those cases when the device is manufactured from a material in which the gliding effect is not easily accomplished. According to this embodiment shown in FIG. 4b, the mixing-reservoir (Ac) has at least two longitudinal guiding grooves, present into the walls of the mixing-reservoir (Ac). FIG. 4c represents a cross-section of the mixing reservoir (Ac) in which four such longitudinal grooves are shown. The mixer-separator (Bc) shown in FIG. 4a, must have a number of protuberances, a cross section of which is given in FIG. 4d. The number of protuberances on the mixer-separator (4a) must be in accordance with the number of longitudinal grooves present in the mixer-reservoir (Ac). When the mixer-separator (Bc) is pushed into the mixing-reservoir (Ac), the same snug fit effect is obtained as in the device illustrated in FIG. 1.

Figure 5:
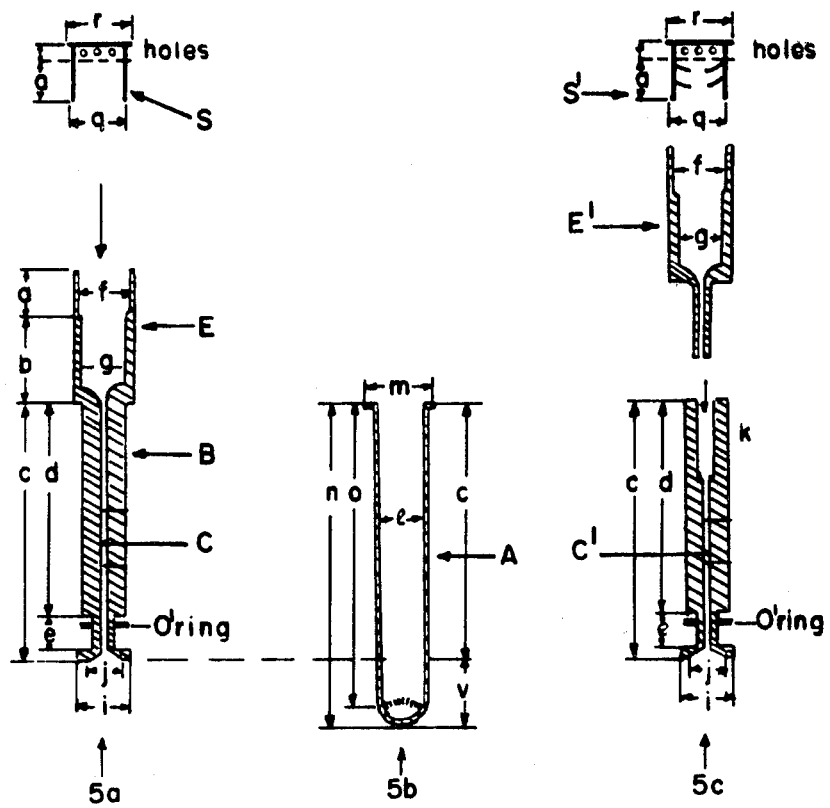
FIG. 5 illustrates yet another embodiment, as shown in FIGS. 5a–c.

FIG. 5 illustrates another embodiment of the device according to the present invention. The device consists again of the four main components: mixing-reservoir (A); mixer-separator (B); collecting container (E) and stopper (S). Two variations are illustrated for the mixer-separator (B). According to one variation, the collecting-container (E) is part of the mixer-separator (B) while according to another variation, the collecting container (E) can be dismantled from the mixer-separator (B). The mixer-separator (B or B') has at its base a sealing element adapted to slide along the inner walls of the mixing-reservoir (A). The sealing element possesses at least one orifice bore passing through its thickness, said bore being connected with the channel (C). Several variations may be encountered in the location and manufacture of the sealing element, without being outside the scope of the present invention. According to one embodiment, the sealing element consists of a rubber O-ring having an orifice bore, adapted to slide along the inner walls of the mixing-reservoir (A). By pushing in the mixer-separator (B), the upper layer liquid is aspirated through the orifice bore and the channel C being accumulated into the collecting container E. According to another embodiment, the rubber O-ring is located slightly above the base of the mixer-separator (B), so that the rubber will not be in contact with the liquid lower phase from the mixing-reservoir (A). In this case no restriction on the type of rubber will be imposed. The stopper (S) which is fitted to close the collecting container (E) or (E') has an inner perforated cover, to enable the entrained drops of liquid to return into the collecting container E through the holes of said cover.

Of course these holes can be of any shape or size without affecting the operation of the device. The operation of the device is similar to that described for FIG. 1.

As already mentioned in the preamble of the specification, the new device according to the present invention can be successfully utilized as a very convenient equipment in the general field of liquid-liquid extraction, either in small scale or in large scale. In small scale it can be utilized in the basic research of solvents screening or in the determination of the limiting condition of the partition coefficients of a given solvent. On large scale it competes very favourably either with the standard mixer-settler or with the known types of columns, due to the efficiency of mass transfer achieved.

Among the main advantages of the device according to the present invention, it should be mentioned the complete absence of hydraulic communication and the separation of the mixing operation from the aspiration function, so that each one may be performed independently according to its own requirements, so that no danger of back-mixing would be encountered. In other words, the device will provide the high efficiency of mass transfer which is obtained generally when a mixer is utilized, but at the same time will be devoided from the disadvantages encountered from a mixer device. The shape of the elements of the new device can be varied as required for any specific case. The volumes of the mixing-reservoir A and collecting container E can be varied as required by the volumes of the two liquid phases involved in the particular separation process. Element E can be a collecting container vessel of any desired geometrical shape and size, provided that at a certain suitable height from the upper end of the mixer separator B, it is wider than the outer diameter of the mixing-reservoir A, if desired to obtain a predetermined quantitative liquid volume collection.

According to one embodiment a ring is interposed between the upper end of the mixing reservoir A and the collecting element E, which can be slided on the mixer-separator B and will thus determine the level of pushing in the mixer-separator B and accordingly the interface between the two liquid phases, thus ensuring a complete removal of the upper phase from the mixing-reservoir A. With the same principle, two or more rings could also be interposed for different positions of interface locations. Such a ring designated by letter D is illustrated in FIGS. 1, 2 and 4.

Another advantage of the method according to the present invention with the novel device is the fact that it can be operated on a series of devices which can be eminently amenable to automation without requiring complicated auxiliary equipment.

The device can be made from any inert material such as glass, polyethylene or any other suitable plastic material and even metal could be considered for some special uses.

The method of separation of two liquid phase according with the present invention will be hereinafter illustrated with a number of examples taken from immunoassay technique, wherein a clear separation is absolutely required, without being limited for this field only.

For the sake of convenience in the following examples we shall refer to the novel Liquid Extraction Separation device according to the present invention as "Lidex" Separators and as "tube A" of the Lidex separator meaning the mixing reservoir A in the description and Figures and "mixer B" of the Lidex separator meaning the whole component B in the description and Figures.

EXAMPLE 1

EXTRACTION EFFICIENCY STUDIES WITH THE LIDEX SEPARATOR USING RADIOISOTOPE TRACERS

In order to determine the suitability of a solvent or mixture of solvents for the extraction of a compound from an aqueous solution the following procedure provided very fast and accurate results. Twelve "tubes A" of the Lidex separator were numbered from 1 to 12. In each "tube A" were added 500 $\mu$l of a EDTA phosphate buffer solution followed by 200 $\mu$l of a solution containing a digoxin derivative labelled with the radioisotope Iodine-125. (This solution was prepared by reconstituting a commercially available digoxin-I-125 derivative (Ames) with 12 ml of the EDTA-phosphate buffer, pH 7.4, containing 1.2 g disodium phosphate and 0.6 disodium EDTA in 100 ml of deionized water). The radioactivity in "tubes A" 1 to 12 was measured in a gamma-counter; each counting was performed twice, each time for 30 seconds. To each "tube A" were then added 1.4 ml of solvents as follows:

(a) Tubes 1 and 2, tert-amyl alcohol; (b) Tubes 3 and 4, a mixture of tert-amyl alcohol/methyl isobutyl ketone (MIBK) at a volume ratio of 9:1; (c) Tubes 5 and 6, tert-amyl alcohol/MIBK, 3:1 (volume ratio); (d) Tubes 7 and 8, tert-amyl alcohol/MIBK, 1:1; (e) Tubes 9 and 10 MIBK and (f) Tubes 11 and 12, tert-butyl ether. (All the above solvents and solvent mixtures had been previously equilibrated with the same EDTA phosphate buffer).

Following addition of the solvents, a mixer-separator B of the Lidex separator was inserted like a stopper into the top of each one of tubes A, 1-12 and each one of these assembled Lidex separators was vortexed for 30 seconds. (By using a suitable tray, all the Lidex separators could be vortexed at the same time). After the Vortex-mixing, the Lidex separators were allowed to stand for 10 minutes, upon which an upper and lower liquid phase were formed. Next, the mixer-separator B of each Lidex separator 1-12 was pushed gently into the "tube A" as far as it could go. (The Lidex separators used in these experiments were constructed so that upon maximum pushing of the mixer separator B, 0.5 ml of the lower liquid phase remained in "tube A", 0.2 ml were in the channel C and all the upper phase (1.4 ml) was in the collecting container E). Each one of the Lidex separators, 1-12 was then placed in the well of the gamma-counter and the radioactivity in the lower phase (remaining in "tube A") was counted as before, twice for each tube, each time for 30 seconds.

The results, as summarized in the following Table 1 show that the precision of the measurements is highly satisfactory. Experiments carried out to determine the accuracy of the measurements, indicated that due to instrumental variations in the well-geometry of gamma-counters there might be up to 1% variation in accuracy of the determination of extraction efficiency.

TABLE 1

Extraction Efficiency determined with Lidex Separators

| Extraction Solvents | Tube No. | Total Counts | Counts in aqueous phase after sepn. | % of remaining radioactivity in aqueous phase | % Extraction efficiency | Mean (± SD) |
|---|---|---|---|---|---|---|
| tert-amyl alcohol/ | 1 | 26264 | 1299 | 4.9 | 95.1 | |
| | 1 | 26131 | 1360 | 5.2 | 94.8 | 94.8 ± 0.2 |
| | 2 | 26770 | 1403 | 5.3 | 94.7 | |
| | 2 | 26442 | 1340 | 5.1 | 94.9 | |
| tert-amyl alcohol/ MIBK (9:1) | 3 | 26165 | 1670 | 6.3 | 93.7 | |
| | 3 | 26219 | 1626 | 6.2 | 93.8 | 94.3 ± 0.6 |
| | 4 | 26178 | 1343 | 5.1 | 94.9 | |
| | 4 | 26350 | 1380 | 5.2 | 94.8 | |
| tert-amyl alcohol/ MIBK (3:1) | 5 | 26397 | 1426 | 5.4 | 94.6 | |
| | 5 | 26631 | 1461 | 5.5 | 94.5 | 94.6 ± 0.1 |
| | 6 | 26474 | 1402 | 5.3 | 94.7 | |
| | 6 | 26073 | 1388 | 5.3 | 94.7 | |
| tert-amyl alcohol/ MIBK (1:1) | 7 | 26104 | 1848 | 7.0 | 93.0 | |
| | 7 | 26291 | 1891 | 7.2 | 92.8 | 93.6 ± 0.9 |
| | 8 | 26215 | 1458 | 5.5 | 94.5 | |
| | 8 | 26797 | 1528 | 5.8 | 94.2 | |
| MIBK | 9 | 26123 | 3332 | 12.7 | 87.3 | |
| | 9 | 26290 | 3308 | 12.6 | 87.4 | 87.3 ± 0.05 |
| | 10 | 26491 | 3347 | 12.7 | 87.3 | |
| | 10 | 26399 | 3312 | 12.6 | 87.4 | |
| tert-butyl methyl ether | 11 | 26191 | 2332 | 8.9 | 91.1 | |
| | 11 | 26592 | 2201 | 8.4 | 91.6 | 90.9 ± 0.7 |
| | 12 | 26032 | 2435 | 9.2 | 90.8 | |
| | 12 | 26311 | 2360 | 10.0 | 90.0 | |

EXAMPLE 2

EXTRACTION EFFICIENCY STUDIES WITH THE LIDEX SEPARATOR USING FLUORESCENT TRACERS

An experiment similar to the one described in Example 1, demonstrated the possibility of using for measurements the upper phase, separated into the collecting container E of the Lidex separator. The data presented describes the use of fluorescent tracers to determine extraction efficiency of solvents but they clearly apply to other determinations, as for example to non-isotopic immunoassays using fluorescent labels or other non-isotopic labelling agents as well as radio-isotopic labels if the free, unbound fraction is to be monitored.

Two standard stock solutions of $5 \times 10^{-4}$M Rhodamine B were prepared, one in doubly distilled water and one in tert-amyl alcohol. These solutions were used for dilution to obtain working solutions of the desired concentrations, $5 \times 10^{-5}$M, $4.5 \times 10^{-5}$M, $4.0 \times 10^{-5}$M, $2.5 \times 10^{-5}$M, $2.25 \times 10^{-5}$M, $2.0 \times 10^{-5}$M, $1.0 \times 10^{-5}$M and $0.5 \times 10^{-5}$M. Calibration curves were obtained with these solutions using a Perkin-Helmer model MPF-44B. Fluorescence Spectrophotometer with an excitation wave length of 430 nm and emission wave length of 615 nm.

Fourteen "tubes A" of the Lidex separator were numbered from 1 to 16. In tubes 1 and 2 as controls were placed 0.7 ml of water. Then in tubes 3 to 16 were placed 0.7 ml of the above working solutions of Rhodamine B in water, each of the above seven concentrations in duplicate. This was followed by the addition of 1.4 ml of tert-amyl alcohol (presaturated with water) to each "tube A" 1 to 16.

A mixer B of the Lidex separator was inserted like a stopper into the top of each one of the "tubes A" and then all the 16 assemblies of the Lidex separators were vortexed for 20 seconds. After allowing to stand for 10 minutes, the mixer B of each assembly 1 to 16 was gently pushed into the "tubes A", as described in Example 1. The upper phase which moved into the collecting container E of each Lidex Separator was poured into a spectrophotometer cell and the fluorescence signal was measured. The concentration of Rhodamine B in each tube was determined from the calibration curve by interpolating the fluorescence signal obtained above and taking into account the dilution factor (2:1) used in the above experiment. The results indicated that extraction of Rhodamine B into the tert-amyl alcohol solvent had occurred to an extent of 90–93% efficiency.

If desired, in the above experiment it would be possible to construct a Lidex separator so that the collecting container E of the mixer B is a separate part, made for instance of quartz or pyrex or other suitable material for fluorescence measurements, and attached to the mixer-separator B prior to the phase separation step. After the phase separation, with the upper phase in the collecting container E, the whole Lidex assembly could be placed into a modified cell holder of the fluorescence spectrophotometer. This would eliminate the step of pouring the upper phase into the cell and the whole operation could be easily automated. As stated in the first paragraph of this Example, the same procedure could be used if, for example, a tritium labelled material had been used as a tracer. Following the phase separation, the upper phase in the collecting container E, into which the tritium-labelled tracer has been extracted, can be poured into the scintillation liquid and taken to a scintillation counter for radioactivity measurements.

EXAMPLE 3

DIGOXIN RADIOIMMUNOASSAY PERFORMED WITH THE LIDEX SEPARATOR

In order to demonstrate the performance, reliability, simplicity, ease of operation and other advantages of the Lidex Separator in immunoassays, two parallel experiments were carried out:

(i) A commercially available kit for digoxin radioimmunoassay RIALYZE ® (Ames) using chromatography tubes as the separation system to separate the free and bound fractions;

(ii) using the same kit reagents, but the assay protocol was based on the use of the Lidex Separator.

All kit components were reconstituted according to the kit directions for use. Duplicate key assay tubes were labelled for Total Counts, Standards A, B, C, D and E. Also, duplicate assay tubes were labelled I, II and III for each DADE control serum (TRI-YAC®, Trilevel Radioimmunoassay Controls, Level I, Level II and Level III).

For the parallel Lidex Separator system, duplicate "tubes A" of the Lidex Separator were labelled for Total Counts, Zero Standard and Standards A, B, C, D and E. Also, triplicate "tubes A" of the Lidex Separator were labelled for each DADE control serum, I, II and III. A volume of 100 μl of the reconstituted I-125 Digoxin reagent was added to all assay tubes. Buffer (50 μl) was added to the Total Counts and Zero Standard assay tubes. To the appropriately labelled standard tubes were added 50 μl of each standard and 50 μl of each control serum were added to the tubes labelled I, II and III.

A volume of 100 μl of reconstituted antiserum was added to all the tubes, except the Total Counts tube to which were added 100 μl of the assay buffer. All tubes were incubated for 20 minutes at room temperature. After the incubation time different procedures were followed for each set:

(i) To each test tube of the RIALYZE kit, a chromatography tube was inserted and allowed to stand for 10 minutes, then 0.8 ml of buffer were added to each test tube and allowed to stand for another 10 minutes. The tubes were then counted for radioactivity in a gamma counter instrument.

(ii) To each "tube A" of the Lidex kit there were added 350 μl buffer (for volume adjustment) followed by the addition of 1.4 ml of the extraction solvent mixture (tert-amyl) alcohol/MIBK in a 3:1 ratio) previously saturated with the assay buffer. A mixer B of the Lidex Separator was inserted like a stopper into the top of each one of the "tubes A" and all the Lidex Separator assemblies were vortexed for 30 seconds.

The assemblies were allowed to stand for 10 minutes (for liquid phases separation) and the mixer B of each Lidex assembly was pushed gently into the tube A as far as it would go. The Lidex assemblies were placed in the well of the gamma counter to measure the radioactivity of the aqueous phase remaining at the bottom of "tube A". The results of the radioactive counting were calculated as Bound/Total for the commercial RIALYZE kit (as prescribed in the kit instructions) and as Bound/Bound zero for the Lidex system.

The results for both experiments were plotted on the kit graph paper on logit scale versus log (digoxin concentration) and are shown in FIG. 6. From the curves on this graph, the digoxin values (ng/ml) of the control sera were determined. The mean values of all the results and composition of the found values for the control sera with these of other commercial kits are summarized in Tables 2 and 3. As can be seen from the graph presented in FIG. 6, and the digoxin concentration values determined for the control sera, the Lidex Separator system gave fully acceptable results for the Digoxin assay.

TABLE 2
COMPARISON BETWEEN IODINE-125 DIGOXIN RADIOIMMUNOASSAY WITH RIALYZE (AMES) KIT AND WITH LIDEX SEPARATOR DEVICE

| Standards | Digoxin Conc. (ng/ml) | RIALYZE KIT Mean % Free (F/T) | LIDEX SEPARATOR Mean % B/Bo |
|---|---|---|---|
| A | 0.6 | 33.6 | 77.0 |
| B | 1.0 | 48.1 | 67.0 |
| C | 2.0 | 65.8 | 46.3 |
| D | 2.8 | 75.7 | 39.3 |
| E | 4.6 | 83.8 | 27.9 |
| Control Sera Level I | | 40.5 | 67.8 |
| Level II | | 61.5 | 47.6 |
| Level III | | 72.7 | 37.6 |

TABLE 3
REFERENCE CONTROL VALUES (ng/ml) CALCULATED FROM RESULTS IN Table 2 AND FIG. 6 and COMPARISON TO PUBLISHED DADE VALUES.

| DADE CONTROLS | RIALYZE KIT (AMES) | LIDEX SEPARATOR | DADE DATA-Tope | RANGE OF VALUES FOR CORNING (I-125) Immunophase | KALESTA D (3H) Quantitope |
|---|---|---|---|---|---|
| Level I | 0.78 | 0.92 | 0.71–1.06 | 0.64–1.04 | 0.77–1.37 |
| Level II | 1.65 | 2.05 | 1.55–2.17 | 1.40–2.10 | 1.48–2.4 |
| Level III | 2.6 | 3.0 | 2.64–3.49 | 2.3–3.5 | 2.33–3.52 |

We claim:

1. A device for carrying out the mass transfer operation of one or more components from a first liquid to a second liquid substantially immiscible with the first liquid and the physical separation of said two liquids, comprising:

a mixing reservoir (A);

a mixer-separator means (B), snuggly fitted into said mixing reservoir for sliding movement therein and having at least one unobstructed channel (C) traversing the vertical axis thereof and opening into said mixing reservoir, and a collection container (E) at the end of said mixer-separator means opposite said unobstructed opening, for thoroughly mixing the two liquids in response to at least one movement of said mixer-separator means into and out of said mixing reservoir by an amount sufficient to cause a substantial portion of both liquids to be transported through said channel into said collection container and back into said mixing reservoir and for subsequently separating the first liquid from the second liquid in response to controlled movement of said mixer-separator means into said mixing reservoir to a distance sufficient to transport the desired amount of the lens dense liquid through said channel into said collection container; and a stopper means (S) on said collection container for selectively opening and closing said collection container to the outside.

2. A device according to claim 1, wherein the mixer-separator (B) has at its base a sealing element which possesses at least one orifice bore passing through its thickness, said bore being connected with the channel (C).

3. A device according to claim 2, wherein the sealing element slides along the inner walls of the mixing-reservoir (A), staying in good contact with said inner walls of the mixing-reservoir (A).

4. A device according to claim 2, wherein said sealing element consists of a rubber-O-ring having an orifice bore connected with the channel C, said ring being adapted to slide along the inner walls of the mixing-reservoir (A).

5. A device according to claim 1, wherein only the lower part of the mixer-separator (B) is snugly fitted into the mixing-reservoir (A).

6. A device according to claim 1, wherein the channel (C) traverses only the lower part of the vertical axis of the mixer-separator (B).

7. A device according to claim 1, wherein the mixing-reservoir (A) possesses at least two longitudinal grooves located into its walls and correspond with the same number of protuberances located on the mixer-separator (B), thus facilitating the gliding of the mixer-separator (B) into the mixing-reservoir (A).

8. A device according to claim 1, wherein the mixing-reservoir (A) has a cylindrical shape.

9. A device according to claim 1, wherein the mixing-reservoir (A) is marked with graduated scale for volume measurements.

10. A device according to claim 1, wherein a ring (D) is interposed between the upper end of the mixing-reservoir (A) and the collecting container (E), which can be slided on the mixer-separator (B), which determines the level of pushing the mixing reservoir (A).

11. A device according to claim 1, wherein the collecting-container (E) is wider than the outer diameter of the mixing-reservoir (A) at a certain height from the upper end of the mixer-separator.

12. A device according to claim 1, wherein said device is made from an inert material.

13. A device according to claim 12, wherein said inert material is selected from the group consisting of glass, polyethylene or any other adequate plastic material and metal.

14. A device according to claim 1, wherein said mixer-separator means is snuggly fitted into said mixing reservoir along the entire length of the mixer-separator means.

15. A method for carrying out mass transfer operation of one or more components from a first liquid to a second liquid substantially immiscible with said first liquid followed by a physical separation of said two liquids, said mass transfer and physical separation operations being carried out in a device as defined in claim 1, said method comprising the steps of:
  introducing two substantially immiscible liquids to be contacted into the mixing-reservoir,
  mixing said liquids by at least one movement of said mixer-separator into and out of said mixing reservoir by an amount sufficient to cause a substantial portion of both liquids to be transported through said channel into said collection container and back into said mixing reservoir;
  allowing an interface to form between the upper phase and lower phase of said two liquids;
  moving the mixer-separator means into the upper phase contained in said mixing reservoir to cause flowing of a desired amount of the liquid upper phase through said unobstructed channel into the collecting container.

16. A method for carrying out mass transfer operation according to claim 15, wherein said liquids are suitable for immunossay.

17. A method for carrying out mass transfer operation according to claim 16, wherein said immunoassay is radioimmunoassay.

18. A method for carrying out mass transfer oepration according to claim 15, wherein said mixing, forming, moving and flowing steps are performed automatically.

19. A method for carrying out mass transfer operation according to claim 15, wherein said liquids in said mixing step contain digoxin.

20. A method for carrying out mass transfer operation according to claim 15, wherein said liquids in said mixing step contain a hormone selected from the group consisting of estradiol, progesterone, and testosterone.

21. A method for carrying out mass transfer operation according to claim 15, wherein said liquids in said mixing step contain $T_4$.

22. A method for carrying out mass transfer operation according to claim 15, wherein said liquids in said mixing step contain $T_3$.

23. A method for carrying out mass transfer operation according to claim 15, wherein said liquids in said mixing step contain barbiturates.

24. A method for carrying out mass transfer operation according to claim 15, wherein said liquids in said mixing step contain cannabinoids.

25. A method for carrying out mass transfer operation according to claim 15, wherein said liquids in said mixing step contain morphine.

26. A method for carrying out mass transfer operation according to claim 16, wherein mass transfer occurs in said mixing step and separation of the bound and free ligands of said immunoassay occurs after said mixing step in said interface forming and said flowing steps.

27. A method for carrying out mass transfer operation according to claim 16, wherein said immunoassay is free radical assay.

28. A method for carrying out mass transfer operation according to claim 16 wherein said immunoassay is fluorescence immunoassay.

29. A method for carrying out mass transfer operation according to claim 16, wherein said immunoassay is enzyme immunoassay.

30. A method for carrying out mass transfer operation according to claim 16 wherein said immunoassay is metalloimmunoassay.

31. A method according to claim 15, wherein said moving step comprises moving the mixer-separator means into the upper phase by an amount sufficient to cause the upper phase to flow through said channel so that substantially none of the upper phase remains in said channel.

32. A kit for immunoassay comprising:
  a device as defined in claim 1;
  a first liquid containing a substance to be assayed; and
  a second liquid substantially immiscible with said first liquid and containing a means to identify said substance to be assayed.

* * * * *